United States Patent [19]

Binder et al.

[11] Patent Number: 4,994,484
[45] Date of Patent: Feb. 19, 1991

[54] 1-(3-(2-HYDROXY-3-ALKYLAMINO-PROPOXY)-2-THIENYL)-3-PHENYL-1-PROPANONES AND PROCESS FOR THE PREPARATION OF THE SAME

[75] Inventors: Dieter Binder, Vienna; Gerhard Greier, Linz, both of Austria

[73] Assignee: Laevosan-Gesellschaft m.b.H., Linz, Austria

[21] Appl. No.: 469,893

[22] Filed: Jan. 24, 1990

[30] Foreign Application Priority Data

Jan. 24, 1989 [AT] Austria .................................. A130/89

[51] Int. Cl.$^5$ ..................... A61K 31/38; C07D 333/32
[52] U.S. Cl. ...................................... 514/445; 549/64
[58] Field of Search ........................... 549/64; 514/445

[56] References Cited

U.S. PATENT DOCUMENTS 4,352,819 10/1982 Binder .................................. 549/64
4,814,330 3/1989 Binder .................................. 549/64

FOREIGN PATENT DOCUMENTS 0266336 5/1988 European Pat. Off. ............... 549/64
3316155 11/1984 Fed. Rep. of Germany ........ 549/64

Primary Examiner—M. Alan Siegel
Attorney, Agent, or Firm—Sughrue, Mion, Zinn, Macpeak & Seas

[57] ABSTRACT 1-(3-(2-hydroxy-3-alkylaminopropoxy)-2-thienyl)-3-phenyl-1-propanones represented by formula (I)

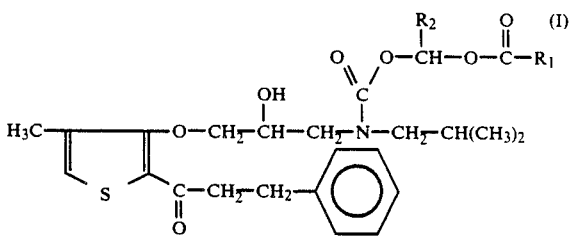

wherein $R_1$ and $R_2$ each represent a lower alkyl group, and a process for the preparation of the same. The compounds of the present invention are useful in the treatment of cardiac arrhythmias.

4 Claims, No Drawings

1-(3-(2-HYDROXY-3-ALKYLAMINOPROPOXY)-2-THIENYL)-3-PHENYL-1-PROPANONES AND PROCESS FOR THE PREPARATION OF THE SAME

FIELD OF THE INVENTION

The present invention relates to drug precursors, i.e., therapeutically valuable 1-(3-(2-hydroxy-3-alkylaminopropoxy)-2-thienyl)-3-pehnyl-1-propanones represented by formula (I)

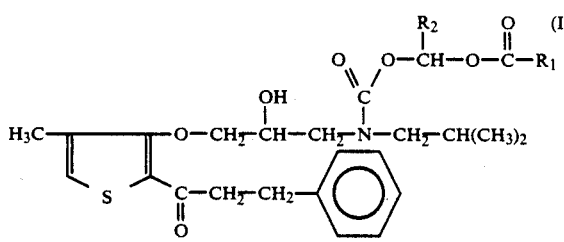

wherein $R_1$ and $R_2$ each represent a lower alkyl, which are useful int he treatment of cardiac arrhythmias; and a process for the preparation of the same.

BACKGROUND OF THE INVENTION

Thienyl derivatives represented by formula (II)

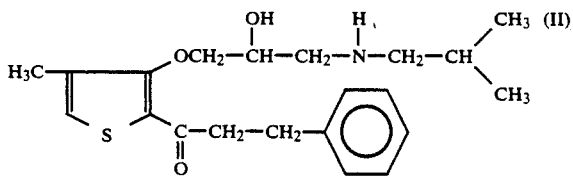

having no substituent on the nitrogen atom, are known. These compounds posses anti-arrhythmic activity in low doses and are orally administered. However, these compounds have a disadvantage in that they can only be resorbed poorly by the body of animals, including man.

SUMMARY OF THE INVENTION

Accordingly, an object of the present invention is to convert the known substances, which are effective in the treatment of cardiac arrhythmias, into compounds which can be resorbed easily by the body of animals, including man, which compounds, however, does not lose the desired pharmaceutical activity.

Another object of the present invention is to provide a process for the preparation of said compounds.

DETAILED DESCRIPTION OF THE INVENTION

It has surprisingly been found in the present invention that compounds having substantially the same anti-cardiac arrythmia activity as that represented by formula (II), are obtained when the amino group is substituted in a manner shown in formula (I) below

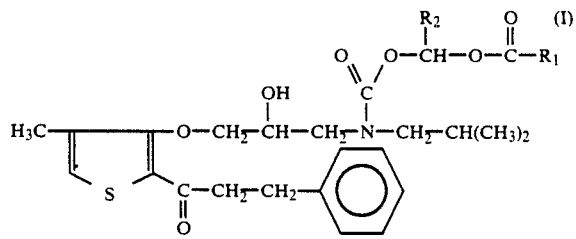

wherein $R_1$ and $R_2$ each represent a lower alkyl group.

The lower alkyl group represented by $R_1$ and $R_2$ generally contains 1-4 carbon atoms, preferably 1 carbon atom.

It is believed that the compounds represented by formula (I), after their resorption, are converted into the compound of formula (II).

Thus, the compounds of the present invention not only have an outstanding effect on cardiac arrhythmias, but can also be substantially better resorbed by the body of animals, including man, than the known compound represented by formula (II).

The compounds of the present invention can be employed in a pharmaceutical composition along with any conventional pharmaceutically acceptable carrier or diluent to produce an anti-cardiac arrythmia composition. Such compositions are also within the scope of the present invention.

The present invention also relates to a process for the preparation of the compounds represented by formula (I) in which a compound represented by formula (II) is reacted with a compound represented general formula (III)

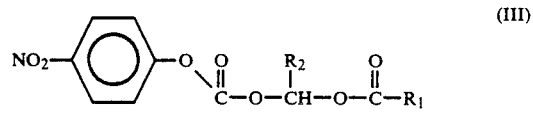

wherein $R_1$ and $R_2$ each represent a lower alkyl group. Preferably, α-acetoxy-ethyl-p-nitrophenyl carbonate is used as the compound represented by formula (III).

The molar ratio of the compound represented by formula (II) to compound represented by formula (III) in the reaction mixture is generally about 1:1, although it is preferred to use a slight excess of the compound represented by formula (II).

The reaction is carried out in an inert polar solvent, such as DMF, dimethyl acetamide, DMSO or hexamethylphosphoric acid triamide. The reaction is generally carried out at 0° C. to 30° C., preferably at room temperature (20° C.); for about 1 to 4 hours, depending on the temperature.

The following example illustrates the process of the invention but is in no way intended to limit the scope of the present invention.

EXAMPLE

A solution of 9.8 g (26.09 mmoles) of 1-(3-(2-hydroxy-3-(2-methylpropylamino) -propoxy)-4-methyl-2-thienyl)-3-phenyl-1-propanone and 7.0g (26.00 mmoles) of α-acetoxyethyl-p-nitrophenyl carbonate in 85 ml of dry hexamethylphosphoric acid triamide was stirred at room temperature for 2 hours.

The reaction mixture was then poured onto 300 ml of water and extracted with ether. The organic phase was washed with a 1.0 N sodium hydroxide solution and water, dried over sodium sulfate and evaporated. 12.89 of an oily residue was obtained which was purified by column chromatography.

Column chromatography: silica gel mobile phase for the 1st column: dichloromethane/ethanol =12/1 mobile phase of the 2nd column: toluene/ethanol =12/1

DC: Mobile phase dichloromethane/ethanol=12/1; Rf=0.65 yield: 11.6 g of a pale-yellow tenacious oil (87.9%)

(q, 1H, O—C$\underline{H}$—CH$_3$),
‖
O

While the invention has been described in detail, and with reference to specific embodiments thereof, it will be apparent to one skilled in the art that various changes and modifications can be made therein without departing from the spirit and scope thereof.

We claim:

1. 1-(3-(2-hydroxy-3-alkylaminopropoxy)-2-thienyl)-phenyl-1-propanones represented by formula (I)

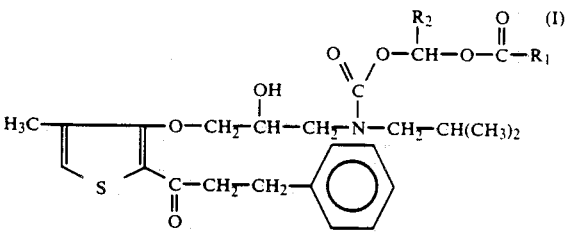

wherein $R_1$ and $R_2$ each represent a lower alkyl group.

2. 1-(3-(2-hydroxy-3-(N-N-(2-methylpropylamino))-propoxy)-4-methyl-2-thienyl)-3-phenyl-1-propanone.

3. An anti-cardiac arrythmia composition comprising a pharmaceutically effective amount of a compound represented by formula (I), as defined in claim 1, and a pharmaceutically acceptable carrier or diluent.

4. The composition as claimed in claim 2, wherein said compound is 1-(3-(2-hydroxy-3-(N-N-(2-methylpropylamino))-propoxy)-4-methyl-2-thienyl)-3-phenyl-1-propanone.

* * * * *